(12) United States Patent
Sarrazin et al.

(10) Patent No.: US 9,683,950 B2
(45) Date of Patent: Jun. 20, 2017

(54) XRD SAMPLE HANDLING APPARATUS

(71) Applicants: Philippe Christian Sarrazin, Sunnyvale, CA (US); Aaron Troy Baensch, Woy Woy Bay (AU); Will M. Brunner, Scotts Valley, CA (US)

(72) Inventors: Philippe Christian Sarrazin, Sunnyvale, CA (US); Aaron Troy Baensch, Woy Woy Bay (AU); Will M. Brunner, Scotts Valley, CA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 123 days.

(21) Appl. No.: 14/877,995

(22) Filed: Oct. 8, 2015

(65) Prior Publication Data

US 2016/0123908 A1 May 5, 2016

Related U.S. Application Data

(60) Provisional application No. 62/073,250, filed on Oct. 31, 2014.

(51) Int. Cl.
*G01N 23/00* (2006.01)
*G01N 23/20* (2006.01)
*G01N 23/207* (2006.01)

(52) U.S. Cl.
CPC ..... *G01N 23/20025* (2013.01); *G01N 23/207* (2013.01); *G01N 2223/056* (2013.01)

(58) Field of Classification Search
CPC ....... G01N 23/20065; G01N 2223/056; G01N 23/207
See application file for complete search history.

(56) References Cited

U.S. PATENT DOCUMENTS

| 7,113,265 B1 * | 9/2006 | Sarrazin | G01N 21/85 356/244 |
| 7,134,459 B2 | 11/2006 | Carlson et al. | |
| 8,302,477 B2 * | 11/2012 | Sarrazin | B01L 9/00 73/579 |
| 2007/0021929 A1 | 1/2007 | Lemmo et al. | |

* cited by examiner

*Primary Examiner* — Dani Fox
(74) *Attorney, Agent, or Firm* — C. Tricia Liu

(57) ABSTRACT

Disclosed is a sample handling assembly facilitating a sample holding cell used for XRD analysis. The assembly holds the sample cell upright during sample loading and analysis phases. The sample handling assembly is vibrated, partly by a tuning fork, to allow the powder to flow into the sample cell. After the XRD analysis, a rotating arm holding the sample cell is rotated 180° to orient the sample cell completely upside down so that the sample can be emptied. Also disclosed are jets of air that are pulsed onto the sample cell, and/or into the sample cell funnel-tube assembly, to shake and clean the components.

18 Claims, 6 Drawing Sheets

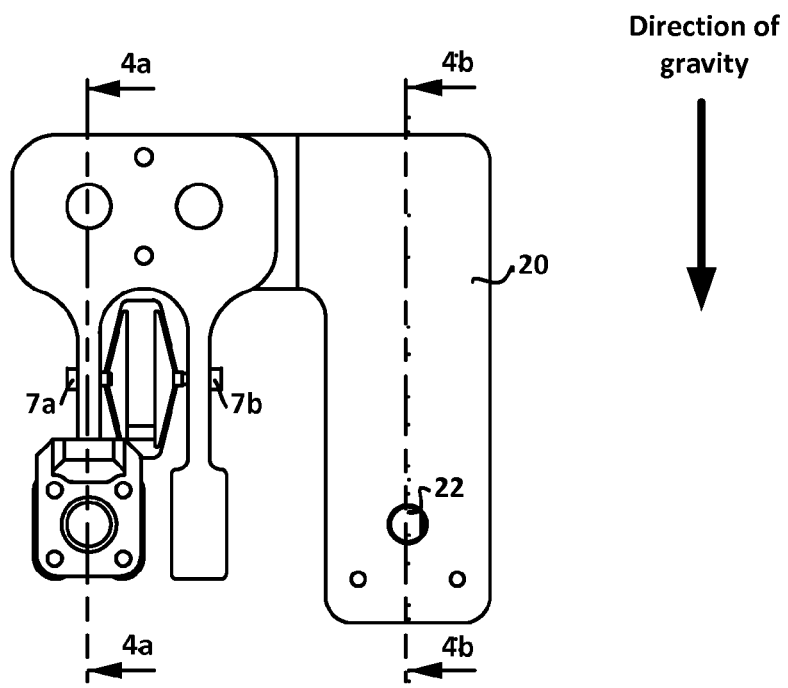
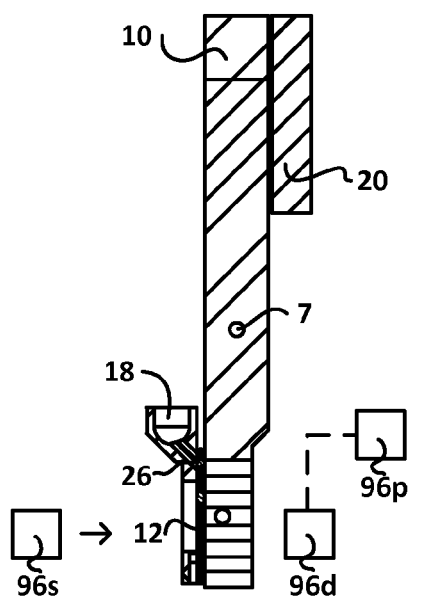
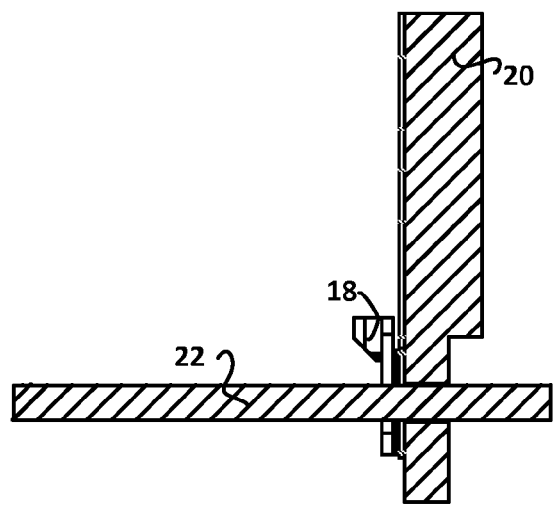
Fig. 3
Fig. 4a
Fig. 4b

XRD SAMPLE HANDLING APPARATUS

CROSS-REFERENCE TO RELATED APPLICATIONS

This application claims the benefit and priority of U.S. Provisional patent application Ser. No. 62/073,250 filed Oct. 31, 2014 entitled AN IMPROVED XRD SAMPLE HANDLING APPARATUS, the entire disclosure of which is incorporated herein by reference.

FIELD OF THE INVENTION

This invention relates to X-ray Diffraction (XRD) instruments, more particularly to an improved sample handling assembly for the loading, analysis, emptying, and cleaning of powder samples in sample cells.

BACKGROUND OF THE INVENTION

X-ray Diffraction (XRD) is a method of analyzing the crystal structure and elemental composition of samples. XRD is used in a wide variety of applications, including the manufacture of pharmaceutical compounds, and industrial characterization of cement and mining materials.

Powder samples of minerals are a practical necessity for XRD, because a very large number of different crystal orientations need to be presented to the incoming X-rays in order to produce a predictable XRD pattern. A further advantage of using powder samples of minerals is that the powder can be moved during analysis when using coarse grained materials, so that all crystalline orientations are evaluated over time. One method for obtaining such powder motion is to use convective sample cells placed under intense vibration in order to generate granular convection movement in the powder during XRD analysis.

In practice, XRD instruments require insertion of powdered samples into a sample cell. The sample cell is then placed on a sample holder, which is introduced into the instrument. After analysis, the sample cell must be replaced or fully emptied of the sample in a manner that prevents cross-contamination. U.S. Pat. No. 7,113,265 B1 discloses the automated use of vibrations to fluidize powder for loading a sample cell, and emptying it. However this patent does not propose a full automation solution for the sample loading and removal.

Previous effort of the present Applicant includes U.S. Pat. No. 8,302,477, herein incorporated by reference in its entirety for all purposes, which teaches creating the vibrational movement by means of a tuning fork, including an actuator, a resonator, a holder arm, and a balancing arm to induce granular convection in a sample during XRD analysis; however, it does not include an assembly for loading and emptying the sample conveniently.

U.S. Pat. No. 7,134,459 B2 discloses a method for preparing a mixed powder sample, including motorized vibration for fluidization, a suction port, a pneumatic blower, and a gas flow control system. However this solution is primarily for mixing powders instead of analyzing them, and uses an array of source and destination wells in place of a single sample holder.

US Pat. No. 2007/0021929 A1 discloses a computerized high-throughput method for sample delivery to instruments, including XRD. This solution is heavily dependent on technology, involving data sets, optimal formulations, robotics, and multiple sample sites, and is not practical for loading and emptying a single sample holder containing mineral powder.

Applicant's co-pending U.S. application Ser. No. 14/313,411, filed on 24 Jun. 2014 and herein incorporated by reference under 37 C.F.R. §1.57(d) in its entirety for all purposes, discloses a sample cell assembly for containing and holding samples for X-ray analysis, which is configured to be attached to a tuning fork assembly for vibrating the samples, and means of locking and unlocking said sample cell assembly. However this solution too does not include a means allowing automatic or semi-automatic loading and emptying the sample conveniently.

Considering the background information above, a simple, robust solution which accepts loose materials loaded into an inlet by the user, and automates a series of operations to transfer the sample, perform the analysis, remove the sample and clean all components that come into contact with the powder samples, would be of great economic value. XRD sample analysis would take place in less time and with more effectiveness.

SUMMARY OF THE INVENTION

It is a general object of the present disclosure to provide a sample handling assembly facilitating a sample holding cell for XRD analysis, with the sample particle size ranging from loose powder to grain. The assembly holds the sample cell upright during the phases of sample loading and analysis. The sample handling assembly is vibrated, partly by a tuning fork to allow the powder to flow into the sample cell. After the XRD analysis, a rotating arm holding the sample cell is rotated 180° so that the sample can be emptied with the sample cell completely upside down.

A funnel or a series of two funnels connecting to a vertical tube is devised to guide the powder to the inlet of a vibrated sample cell. The funnel-tube assembly is optionally vibrated, by a non-concentric motor, and the vertical tube has mechanical impulses applied, preferably by a thwacker sub-assembly, to allow the powder to flow into the sample cell. XRD analysis is performed once the sample cell is properly located in the optical path of the measurement instrument and a predetermined amount of powder is loaded into the cell. After analysis, an arm holding the sample cell is rotated to place the sample cell in an upside down position. The sample is emptied with the assistance of gravity and the vibration of the tuning fork. Furthermore, jets of air are pulsed on the sample cell window, and/or into the funnel-tube assembly, to clean the components. Vacuum suction is provided in places where the sample flows down to ensure the evacuation of all of the powder. After cleaning, the arm is rotated back to its initial position to allow the next sample to be loaded.

BRIEF DESCRIPTION OF THE DRAWINGS

FIG. 3 is an elevation view of the present disclosure, showing the sample handling assembly at the loading position.

FIG. 4a is a cross section view of the present disclosure, showing the sample handling assembly at the loading position.

FIG. 4b is another cross section view of the present disclosure, showing and the sample handling assembly at the loading position, and the swing arm assembly.

DETAILED DESCRIPTION OF THE INVENTION

Figure 1:
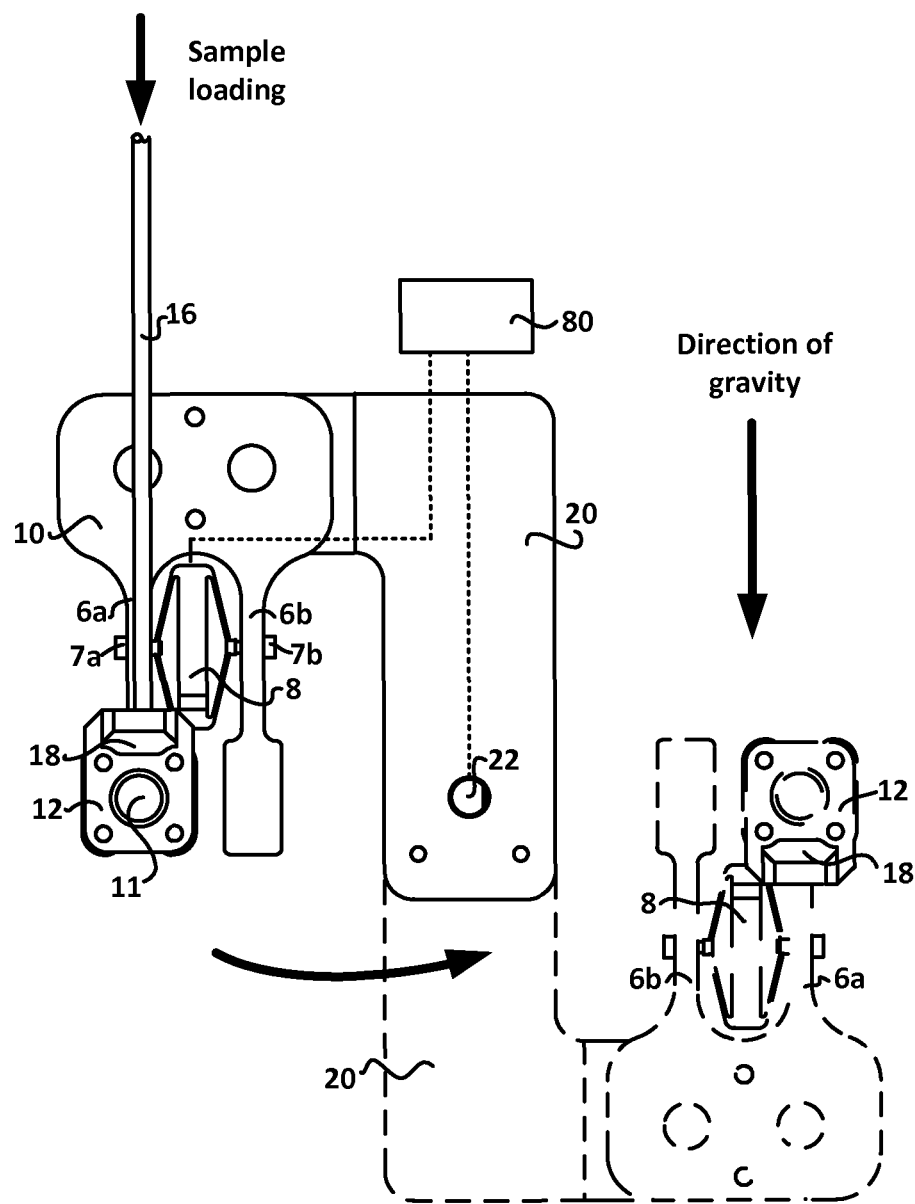
FIG. 1 is an elevation view of the present disclosure, showing the present disclosure both in the loading and unloading positions.
Figure 2:
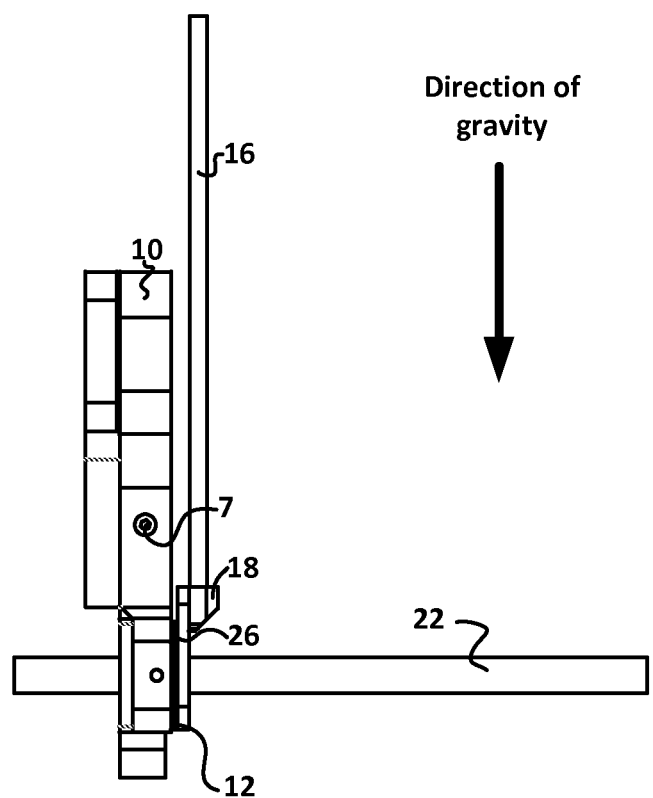
FIG. 2 is an elevation view of the present disclosure, showing the swing arm assembly.

Referring to FIGS. 1 and 2, an XRD sample handling assembly is shown to be configured for serving sequential functions of sample filling, holding and removing or emptying in order for an XRD analysis to be conducted on the sample. In FIG. 1, with reference to the direction of gravity, the portion depicted in solid lines shows the assembly in an upright sample loading and XRD analyzing phase. The portion depicted in dashed lines shows the assembly in a sample removing phase.

As shown in FIG. 1, the sample handling assembly comprises a sample feeding tube 16, a rotating arm 20, a rotation shaft 22, a sample transfer funnel 18 and a sample cell 12, which further comprises a cell window 11 and a sample cell opening 26 (later shown in FIG. 4a). The sample handling assembly further comprises a tuning fork subassembly, which further comprises a tuning fork base 10, a tuning fork sample arm 6a, a tuning fork balancing arm 6b, and a piezoelectric actuator 8, wherein sample cell 12 is attached to and held by one end of sample arm 6a.

Sample arm 6a functions as one prong of a tuning fork which vibrates during the powder loading, analyzing, and unloading processes. As can be seen, the tuning fork subassembly, attached to a piezoelectric actuator 8 by fasteners 7a and 7b, holds sample cell 12 in place for the duration of the sample loading, XRD analysis and sample unloading cycle. While vibrating, the sample handling assembly loads sample powder from sample feeding tube 16. Sample transfer funnel 18 envelopes the bottom of sample feeding tube 16 and receives the sample from it to guide the sample into sample cell 12.

At the starting position, piezoelectric actuator 8 is turned on to vibrate the sample handling assembly. In the preferred embodiment of the disclosure, sample material in the form of powder or loose grain is dropped from sample feeding tube 16 to flow down into sample cell 12 for analysis.

Still referring to FIG. 1, the sample loading into sample feeding tube 16 is optionally and preferably assisted by an auxiliary shaking or vibrating means, such as a thwacker device 60b later shown in FIG. 6. Details on an exemplary embodiment of the shaking means are later described in association with FIG. 6.

It should be noted that sample feeding tube 16 and sample transfer funnel 18 are intentionally detached so that sample transfer funnel 18 rotates together with sample cell 12 to the removing phase. This is also the reason an auxiliary shaking means is provided to sample feeding tube 16, since the vibration from tuning fork sample arm 6a and tuning fork balancing arm 6b does not transfer to sample feeding tube 16.

In FIG. 2, the side view of FIG. 1, rotation shaft 22 is clearly shown. It should be appreciated that the mechanism which rotates the sample cell upside down for sample dropping and removing can be achieved by many mechanical implementations. One of the novel aspects of the present disclosure is that rotation of sample cell 12 is achieved by rotation of the whole tuning fork assembly. And yet the rotation of sample cell 12 is only one of the exemplary embodiments herein shown, and should not be viewed as restrictive to the scope of the present disclosure.

For example, although not shown, sample cell 12 can also be configured in such a way that, instead of being flipped upside down, there is a second opening opposite to the opening for receiving the loaded sample, so that during the sample removing phase, the second opening can be opened for the sample to flow out. Such alternation should also be considered to be within the scope of the present disclosure.

An important aspect of the present disclosure is use of the tuning fork assembly during the sample filling and removing phase of the XRD analysis to assist the fluidity of the samples; in contrast, the tuning fork used in prior art U.S. Pat. No. 8,302,477 as discussed in the "Background" section is mainly for the purpose of causing sample convection in order to provide a full spectrum of diffracted angles from an incident beam of X-rays for XRD analysis.

Reference is now made to FIG. 3, together with FIGS. 4a and 4b, wherein the sampling handling assembly at the loading position is shown with cross-sectional views. FIG. 4a shows a cross-sectional view of tuning fork base 10, sample transfer funnel 18, and rotating arm 20. Fasteners 7a and 7b (shown in FIG. 3) pass through a hole 7. FIG. 4b shows a second cross-sectional view of sample transfer funnel 18, rotating arm 20, and rotation shaft 22.

Also shown in FIG. 4a is that, in one embodiment, the sample handling assembly is configured to locate sample cell 12 in the optical path between an X-ray source 96s and an X-ray detector 96d. It should be noted that the optical path shown in FIG. 4a between X-ray source 96s and X-ray detector 96d is a through-transmission configuration in which source and detector face each other with sample cell 12 in the middle. Alternatively, the optical path between X-ray source 96s and X-ray detector 96d can also be a reflection configuration (not shown) in which source and detector both face sample cell 12 from the same side, and the optical path angle of each with respect to a location on the surface of cell window 11 may be different. Both the through-transmission and reflection configurations are within the scope of the present disclosure.

As further shown in FIG. 4a, X-ray detector 96d is also configured to be coupled with a signal and data processor 96p for analyzing the X-ray response from the sample received via detector 96d.

Figure 5A:
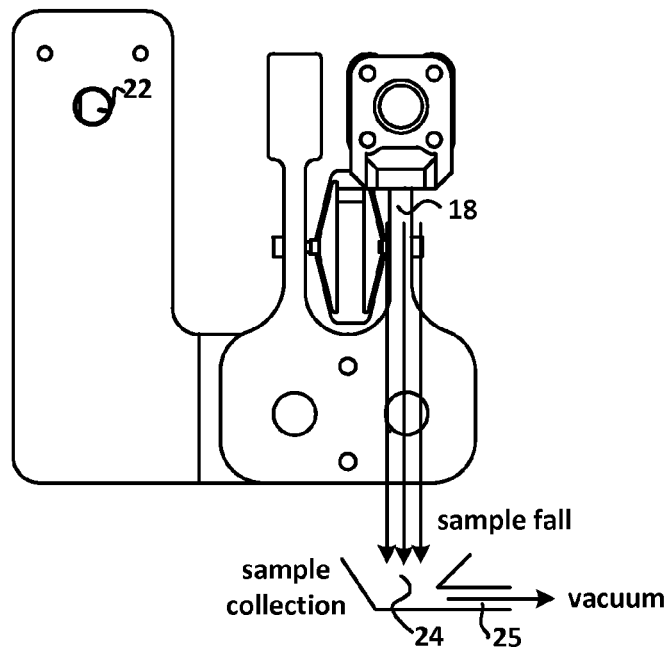
FIGS. 5a and 5b show the cleaning operation of the present disclosure with the sample handling assembly at the unloading position.

Referring to FIG. 5a, the sample handling assembly is shown at the sample removing phase, with optional auxiliary means for efficient sample removal. After analysis of the sample, a vacuum means (device not shown, air-stream exhibited by arrowed lines) is turned on, and the sample handling assembly is flipped upside down on rotation shaft 22, with the sample handling assembly at the sample removal position. The rotation of the assembly is powered by an electric motor. The electric motor is controlled by a computer combined with an encoder and/or position switches, or is limited mechanically by bump stops at either end. It should be appreciated that the use of motors, position switches and bump stops are well known in the practice of mechanical design. All variations of designs enabling the flipping of the sample handling assembly are within the scope of the present disclosure.

The continued vibration of the tuning fork assembly fluidizes the sample so that it falls down by gravity through sample transfer funnel 18. An auxiliary air flow is then applied to the opening of sample transfer funnel 18 and sample cell 12 to ensure evacuation of the sample. A nozzle (not shown) is placed under the area of powder removal to collect the sample falling down onto a purging tray 24. The sample is then permanently removed by the vacuum stream through a purging tube 25.

Figure 5B:
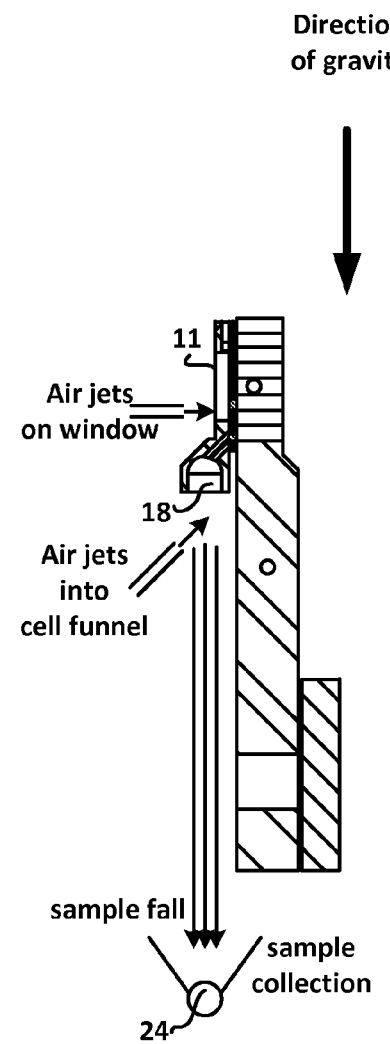

Reference is now made to FIG. 5b. Once most of the sample material has been removed, the sample handling assembly is cleaned by applying air jet pulses onto cell window 11 and/or into sample transfer funnel 18. The air jet pulses are repeated a predefined number of times (exemplary instance 5 times, exemplary duration 1 second), the repetition and duration of the pulses being controlled by electromechanical valves controlled by a computer. The pulsed air jets are powered by an air compressor, or another source of pressurized air that is within the scope of the present disclosure.

Blowing pulsed air on cell window 11 while the cell is being vibrated improves the efficiency of powder removal. The pulsed air does not go inside the cell, but instead applies pressure on the window surface which breaks agglomerated powder that might have formed inside sample cell 12. Referring to Applicant's co-pending U.S. application Ser. No. 14/313,411, herein incorporated by reference, window 11 is of a thin film structure, which vibrates upon receiving air bursts.

Residual powder in the tube and from sample transfer funnel 18 is removed using air jet pulses directed into sample transfer funnel 18, combined with suction from the vacuum applied at purging tray 24. The air jet pulses at sample transfer funnel 18 are also fixed in duration and number, and can be timed parallel to the air jet pulses that are cleaning cell window 11.

Still referring to FIG. 5b, the air-jet pulses that blow toward sample transfer funnel 18 force air inside sample cell 12 via the channel between the inside of the cell and the sample transfer funnel, causing the windows to bulge out due to increased internal air pressure, and to loosen agglomerates of powder that might be stuck between the windows. The pulsed air jets going in and coming out of sample cell 12 further flush out small particles.

Referring back to FIG. 1, with the sample cell and sample transfer funnel-tube assembly clean, both the vacuum means, and piezoelectric actuator 8 for the tuning fork assembly, are turned off. The sample handling assembly is rotated back to the starting position, and the apparatus is ready to receive the next batch of sample.

Figure 6:
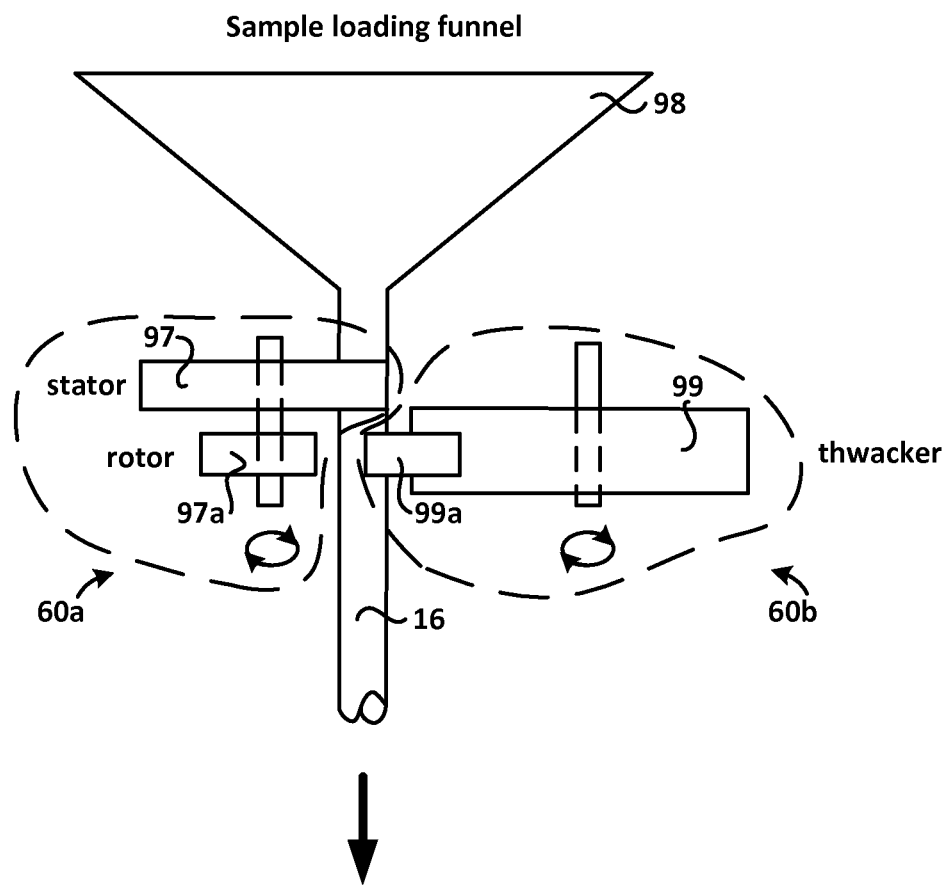
FIG. 6 is an elevation view of the loading funnel shaking means.

Referring now to FIG. 6, the sample handling assembly further comprises a sample loading funnel 98 which loads samples into sample feeding tube 16 shown in FIG. 1. The sample handling assembly optionally, yet preferably, comprises a shaking means for sample loading funnel 98 and sample feeding tube 16. Shaking can be in the form of a non-concentric shaker 60a and/or thwacker 60b. Non-concentric shaker 60a comprises a stator 97 and a rotor 97a. Thwacker 60b comprises a rotor 99 and a thwacker arm 99a.

At the starting of sample loading, non-concentric shaker 60a, thwacker 60b and piezoelectric actuator 8 (shown in FIG. 1) are turned on to vibrate the sample handling assembly to facilitate the flow of the sample powder. In the preferred embodiment of the present disclosure, sample material in the form of powder or loose grain is provided to sample loading funnel 98 to be dispensed into sample feeding tube 16 to flow down towards sample cell 12 for analysis. More specifically, stator 97 achieves its wobbling function by means of rotor 97a, which is mounted off center with respect to its rotational axis and rotated by a motor (not shown). Stator 97 then subsequently applies a wobbling force to sample feeding tube 16 to facilitate the flow of the sample powder from sample loading funnel 98 into sample feeding tube 16.

Alternatively, thwacker 60b imparts a mechanical impact by means of thwacker arm 99a to assist the flow of powder as well. Thwacker arm 99a is preferably spring loaded to allow it to be in position to thwack sample feeding tube 16, and then move out of the way of sample feeding tube 16 to rotate 360°, in order to apply the next thwack with thwacker arm 99a returned to its thwacking position.

Referring back to FIG. 1, the sample handing assembly optionally includes a computerized controller module 80, which can be configured to control piezoelectric actuator 8, and actuate rotating arm 20 and other auxiliary devices as introduced above, such as non-concentric shaker 60a, thwacker 60b, and the vacuum means.

Figure 7:
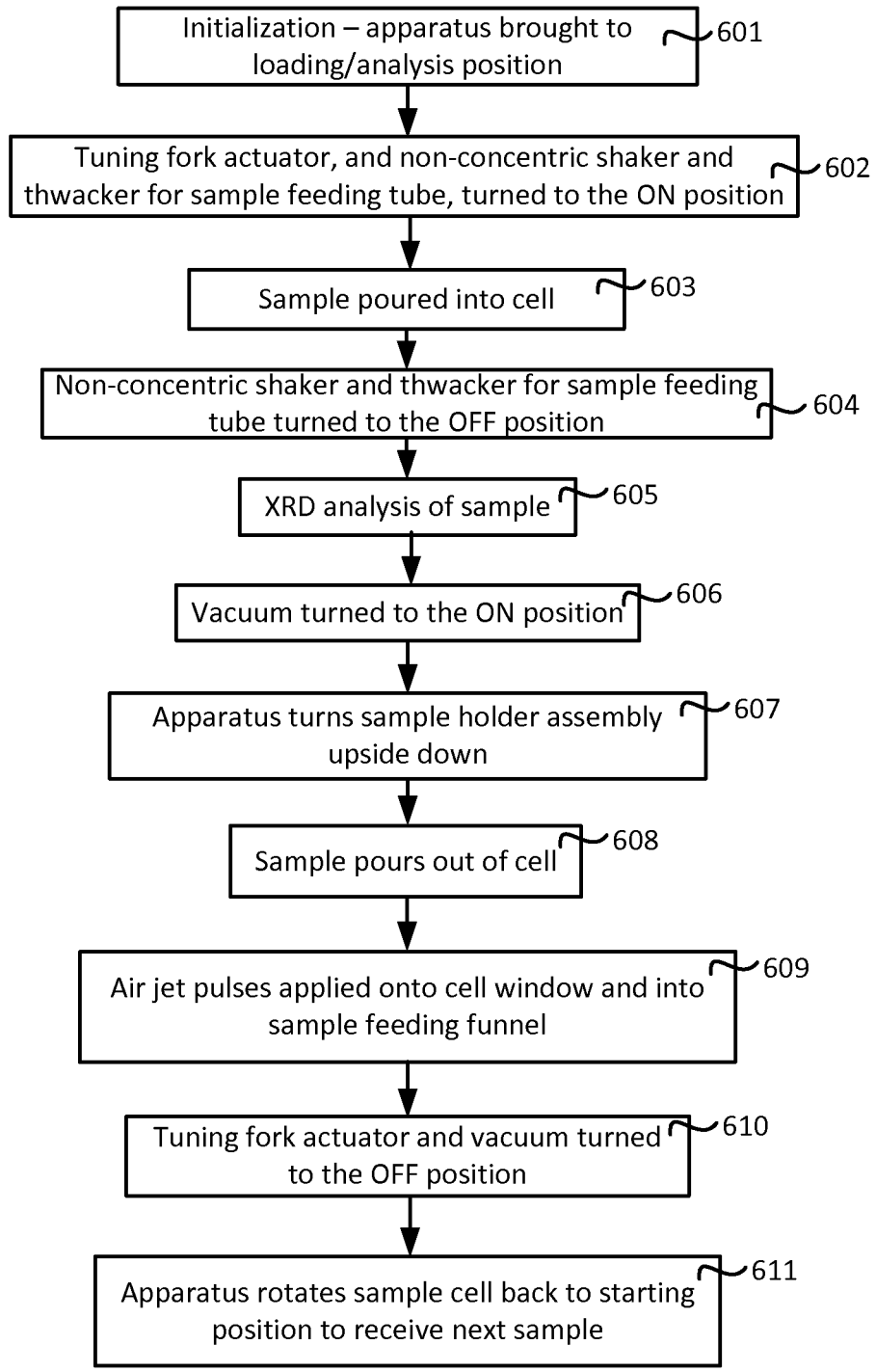
FIG. 7 is a flow chart of the procedural steps involved with the loading, analyzing, unloading, and cleaning of the present disclosure.

Reference is now made to FIG. 7, which is a flowchart of the operational steps of the sample handling assembly at starting, loading, analysis, flipping, cleaning, and returning back to the starting position. In step 601, initialization occurs, and the sample handling assembly is brought to the loading position for analysis. In step 602, piezoelectric actuator 8 for the tuning fork assembly, the non-concentric shaker 60a, and the thwacker sub-assembly 60b for sample feeding tube 16, are turned on. In step 603, the sample is poured into sample cell 12 via sample feeding tube 16. In step 604, the rotary thwacker and the non-concentric shaker devices for sample feeding tube 16 are turned off. In step 605, XRD analysis of the sample occurs. In step 606, the vacuum for purging tray 24 and purging tube 25 is turned on, and in step 607 the sample holder assembly is turned upside down by the apparatus. In step 608, with continued vibration of the tuning fork assembly, the sample pours out of sample cell 12 through sample transfer funnel 18 onto purging tray 24. In step 609, air jet pulses are applied onto cell window 11 and into sample transfer funnel 18. In step 610, piezoelectric actuator 8 for the tuning fork assembly, and the vacuum, are turned off. In step 611, the apparatus rotates sample cell 12 back to the starting position, ready to receive the next sample.

Although the present invention has been described in relation to particular embodiments thereof, many other variations and modifications and other uses will become apparent to those skilled in the art. For example, the methods to facilitate the motion of the sample powder into sample cell 12, including flipping sample cell 12, applying vibration to feeding tube 16 and loading funnel 98, and applying vibration and air bursts to sample cell 12 and transfer funnel 18, can be conducted in a continuous or non-continuous manner, simultaneously or sequentially, automatically or semi-automatically, or in any combination thereof. It is preferred, therefore, that the present invention not be limited by the specific disclosure herein, but only by the appended claims.

What is claimed is:

1. A sample handling assembly configured to hold at least one sample cell for undergoing an X-ray Diffraction (XRD) analysis operation on a sample in the form of powder or grains contained in the sample cell during the analysis operation, the operation including a sample feeding phase, analysis phase and sample removing phase, the assembly comprises,
at least one sample cell having a sample cell opening and a sample cell window, a sample transfer funnel configured to be on top of the sample cell opening and to guide and transport the sample into the sample cell via the sample cell opening during the sample feeding phase, a tuning fork base, a tuning fork sample arm to which the sample cell is attached, a tuning fork balancing arm, and a tuning fork actuator, wherein the tuning fork sample arm and the balancing arm are both attached to the fork base, a rotating arm to which the tuning fork base is attached, wherein the rotating arm is in a first position causing the cell opening to be facing upward during the feeding and the analysis phases, and rotates upside down to a second position causing the cell opening to be facing downward to allow sample flow out from the sample cell onto a sample tray during the sample removing phase.

2. The sample handling assembly of claim 1, wherein the tuning fork actuator is configured to cause the tuning fork sample arm and the balancing arm to vibrate, thereby causing the sample cell to vibrate to generate convection in the sample during the analysis phase.

3. The sample handling assembly of claim 1, wherein the tuning fork actuator is configured to cause the tuning fork sample arm to vibrate, thereby causing the sample cell to vibrate to shake down the sample during the removing phase.

4. The sample handling assembly of claim 1 further comprising a rotating shaft around which the rotating arm and consequently the sample cell are rotated 180 degrees between the feeding and analysis phase and the removing phase.

5. The sample handling assembly of claim 1, wherein the actuator is attached to, and sandwiched between the fork sample arm and the balancing arm.

6. The sample handling assembly of claim 1 further comprising a sample loading funnel and a filling tube, the filling tube having a higher end attached to a sample loading funnel and a lower end.

7. The sample handling assembly of claim 6 wherein the lower end of the filling tube is positioned right above, yet detached from the sample transfer funnel during the sample feeding and analysis phases.

8. The sample handling assembly of claim 6 further comprising a shaking means configured to shake the filling tube and the loading funnel to assist the sample motion down the filling tube.

9. The sample handling assembly of claim 8, wherein the shaking means is a non-concentric shaker including a stator and a non-concentric rotor.

10. The sample handling assembly of claim 8, wherein the shaking means is a thwacker device including a rotor and a thwacker arm.

11. The sample handling assembly of claim 1 further comprising an air suction means to remove the sample from the sample tray.

12. The sample handling assembly of claim 1 further comprising a first air bursting means to burst air into the sample transfer funnel and consequently into the sample cell during the removing phase.

13. The sample handling assembly of claim 1 further comprising a second air bursting means to burst air onto the sample cell window during the removing phase.

14. The sample handling assembly of claim 1 further comprising a computerized controller module configured to control and actuate at least one of the following:
a) the tuning fork actuator,
b) the rotating arm between the first and the second positions.

15. A method of facilitating at least one sample cell for undergoing an X-ray Diffraction (XRD) analysis operation on a sample in the form of powder or grains and contained in the sample cell during the analysis operation, the operation including a sample feeding phase, analysis phase and sample removing phase, the at least one sample cell is attached to a prong of a tuning fork, the method comprises the steps of,
holding the at least one sample cell in an upright position, with a sample cell opening open and facing upward to receive the sample during the sample feeding phase, actuating the tuning fork to cause vibration of the sample cell, feeding the sample via a sample transfer funnel configured to guide the sample into the sample cell via the sample cell opening while the tuning fork is in vibration, performing XRD analysis on the sample, keeping the tuning fork in vibration, rotating the sample cell upside-down so that the sample cell opening is facing downward in the direction of gravity, allowing the sample to fall down during the sample removing phase, keeping the tuning fork in vibration, returning the sample cell back to the upright position for another cycle of analysis operation.

16. The method of claim 15 wherein the step of actuating the tuning fork is done by an actuator which is attached to, and sandwiched between a fork sample arm and a balancing arm of the tuning fork.

17. The method of claim 15 further including the steps of,
a) filling the sample into a sample loading funnel,
b) allowing the sample to move down through a filling tube by a shaking means, and
c) transferring the sample into the sample transfer funnel.

18. An X-ray Diffraction (XRD) device comprising an X-ray source, an X-ray detector and a data processor and analyzer and at least one sample cell to be exposed to the X-ray source, the XRD device further comprises,
a sample handling assembly configured to hold at least one sample cell for an XRD analysis operation on a sample in the form of powder or grains contained in the sample cell during the analysis operation, the operation including a sample feeding phase, analysis phase and sample removing phase, the assembly comprises,
a sample transfer funnel configured to be on top of a sample cell opening and to guide and transport the sample into the sample cell via the sample cell opening during the sample feeding phase, a tuning fork base, a tuning fork sample arm to which the sample cell is attached, a tuning fork balancing arm, and a tuning fork actuator, wherein the tuning fork sample arm and the balancing arm are both attached to the fork base, a rotating arm to which the tuning fork base is attached, wherein the rotating arm is in a first position causing the sample cell opening to be facing upward during the feeding and the analysis phases, and rotates upside down to a second position causing the cell opening to be facing downward to allow sample flow out from the sample cell during the sample removing phase.

\* \* \* \* \*